US012564388B2

(12) United States Patent
Lee et al.

(10) Patent No.: US 12,564,388 B2
(45) Date of Patent: Mar. 3, 2026

(54) PHASE CHANGE INSERT FOR ULTRASOUND IMAGING PROBE

(71) Applicant: GE Precision Healthcare LLC, Wauwatosa, WI (US)

(72) Inventors: Warren Lee, Niskayuna, NY (US); Naveenan Thiagarajan, Clifton Park, NY (US); Caitlin Strobel, New Castle, PA (US)

(73) Assignee: GE Precision Healthcare, LLC, Wauwatosa, WI (US)

( * ) Notice: Subject to any disclaimer, the term of this patent is extended or adjusted under 35 U.S.C. 154(b) by 101 days.

(21) Appl. No.: 17/583,473

(22) Filed: Jan. 25, 2022

(65) Prior Publication Data

US 2023/0233192 A1     Jul. 27, 2023

(51) Int. Cl.
*A61B 8/00* (2006.01)
*A61B 18/00* (2006.01)
*G12B 15/06* (2006.01)

(52) U.S. Cl.
CPC ............ *A61B 8/546* (2013.01); *A61B 8/4444* (2013.01); *A61B 8/461* (2013.01); *A61B 8/5207* (2013.01); *A61B 2018/00089* (2013.01); *A61B 2560/0406* (2013.01); *G12B 15/06* (2013.01)

(58) Field of Classification Search
CPC ....... A61B 8/546; A61B 8/4444; A61B 8/461; A61B 8/5207; A61B 2018/00089; A61B 2560/0406; A61B 8/483; G12B 15/06
See application file for complete search history.

(56) References Cited

U.S. PATENT DOCUMENTS

| | | | |
|---|---|---|---|
| 7,308,828 B2 | 12/2007 | Hashimoto | |
| 10,206,658 B2 | 2/2019 | Lee et al. | |
| 10,772,603 B2 | 9/2020 | Spicci et al. | |
| 2004/0002655 A1* | 1/2004 | Bolorforosh | ............. B06B 1/06 |
| | | | 600/459 |
| 2008/0188755 A1* | 8/2008 | Hart | ......................... A61B 8/00 |
| | | | 600/459 |
| 2013/0301395 A1* | 11/2013 | Hebrard | ................. A61B 8/546 |
| | | | 367/189 |
| 2014/0360274 A1* | 12/2014 | Cho | .................... G01N 29/0654 |
| | | | 73/644 |

(Continued)

FOREIGN PATENT DOCUMENTS

| | | | | |
|---|---|---|---|---|
| EP | 2124752 B1 * | 4/2019 | ............... | A61B 8/00 |
| WO | WO-2019185478 A1 * | 10/2019 | ........... | A61B 8/4236 |

*Primary Examiner* — Joel Lamprecht
*Assistant Examiner* — James F McDonald, III
(74) *Attorney, Agent, or Firm* — Boyle Fredrickson, S.C.

(57) ABSTRACT

An ultrasound imaging device or an ultrasound imaging probe includes an imaging device including at least one heat generating component and at least one thermal energy storage insert spaced from and disposed in thermal contact with the imaging device, the at least one thermal energy storage insert containing a phase change material (PCM) therein. The thermal energy storage insert is manufactured to closely confirm to a shape of a space defined within the interior of the probe. A method of forming the ultrasound imaging probe includes the steps of manufacturing a thermal energy storage insert from a thermally conductive material, filling the thermal energy storage insert with a phase change material (PCM) and positioning the thermal energy storage insert within an interior of the probe.

11 Claims, 12 Drawing Sheets

(56)               References Cited

U.S. PATENT DOCUMENTS

| | | | |
|---|---|---|---|
| 2015/0351727 A1* | 12/2015 | Nieminen | A61B 8/4455 |
| | | | 600/459 |
| 2016/0077059 A1* | 3/2016 | Chung | G01N 29/326 |
| | | | 73/620 |
| 2017/0164926 A1 | 6/2017 | Spicci et al. | |
| 2018/0263604 A1* | 9/2018 | Manning | A61B 8/546 |
| 2020/0022714 A1* | 1/2020 | Corl | A61B 17/2258 |
| 2020/0093463 A1* | 3/2020 | Sams | A61B 8/4483 |
| 2020/0178941 A1 | 6/2020 | Thiagarajan et al. | |

* cited by examiner

PHASE CHANGE INSERT FOR ULTRASOUND IMAGING PROBE

BACKGROUND OF THE INVENTION

Embodiments of the present disclosure relate generally to ultrasound imaging probes and, more particularly, to heat dissipating structures of ultrasound imaging probes.

Various medical conditions affect internal organs and bodily structures. Efficient diagnosis and treatment of these conditions typically require a physician to directly observe a patient's internal organs and structures. On many occasions, imaging using an ultrasound imaging system is utilized to obtain images of a patient's internal organs and structures in a minimally invasive manner. The ultrasound images can be obtained utilizing a probe that is located either externally or internally relative to the patient.

By way of example, ultrasound images for non-interventional procedures, such as those obtained for transthoracic echocardiography (TTE), can be obtained by placing the probe against the exterior of the chest of the patient when operating the ultrasound imaging system. Alternatively, ultrasound images for interventional procedures, such as for transesophageal echocardiography (TEE) and/or intracardiac echocardiography (ICE), are obtained by inserting the probe within the body of the patient, e.g., into the esophagus, while the ultrasound imaging system is in operation.

Ultrasound procedures are typically performed in examination, intervention and operating room (open heart surgery) situations where imaging of internal structures of the patient is required. The device utilized in performing the ultrasound procedure typically includes the probe, a processing unit, and a monitor. The probe is connected to the processing unit which in turn is connected to the monitor. In operation, the processing unit sends a triggering signal to the probe. The probe then emits ultrasonic signals via an imaging element within the probe into the patient. The probe then detects echoes of the previously emitted ultrasonic signals. Then, the probe sends the detected signals to the processing unit which converts the signals into images. The images are then displayed on the monitor.

Typically, during the operation of the ultrasound imaging system, the emission of the ultrasonic signals via an imaging element disposed at or near the tip of the probe generates an amount of heat from the imaging element within the probe. In addition, some advanced probes contain application specific integrated circuits (ASICs) with electronics for transmitting and receiving signals from the imaging element. These ASICs also dissipate power and generate heat. Further, the more power utilized by the imaging element and associated ASIC to emit the ultrasonic signals, which enhances the quality of the obtained images, the more heat is generated by the imaging element and ASIC. In order to dissipate the heat and comply with regulatory requirements limiting the maximum temperature of the probe, prior art probes include a plastic housing around the tip of the probe that enables the heat to be passively conveyed through the housing and into the ambient environment around the probe, e.g., the air and/or patient skin for an externally positioned probe, or the esophagus tissue for an internally disposed probe. During operation, the heat generated by the imaging device, such as a matrix array transducer and associated application-specific integrated circuit (ASIC), can be conducted directly to and through the housing, such as directly through a plastic acoustic lens forming a part of the plastic housing, or through an acoustic backing layer to a heat sink disposed within the probe housing and thermally coupled between the imaging element and the housing, e.g., by a heat spreader which also functions as an electromagnetic interference (EMI) shield, to direct or conduct heat away from the imaging element.

Plastic is primarily utilized for the probe housing construction for its ability to electrically insulate the interior components of the probe from the patient for safety purposes. However, while heat can be conveyed through the plastic housing, the low thermal conductivity of the plastic material forming the housing places significant restrictions i.e., resistance, on the amount of heat generated by the imaging device that can be dispersed by the plastic housing. In addition, to enhance the robustness of the probe and to accommodate the required creepage distance for electrical insulation purposes, in many probes the plastic housing is formed to be relatively thick, increasing the durability of the probe but consequently also increasing the thermal resistance of the housing and therefore inhibiting heat transfer out of the probe.

Also, the heat sink is thermally coupled to the imaging device and to the heat spreader. The heat spreader must be bonded to the outer plastic housing with an adhesive, adding more thermal resistance to the conduction of heat away from the imaging device through the housing. As such, the power output of prior art probes, and corresponding image quality, is necessarily reduced by the thermal resistance of prior art probe structures.

In addition, while various active cooling systems have been developed for placement within the probe to increase the amount of heat dissipation capable for the probe beyond the capabilities of the passive dissipation achieved through the housing, these cooling systems greatly increase the complexity and associated cost of the probe construction. Further, for interventional or internal probes, the size of the probe required for insertion within the body of the patient, i.e., into the esophagus, does not have space available for a cooling system to be positioned within the probe housing.

Therefore, it is desirable to develop a structure for an ultrasound probe that increases the heat capacity of the probe when in operation. The improved or increased heat capacity of the probe structure allows an increased amount of heat generated by the probe to be absorbed by the probe without affecting the operation of the probe. The increase in the heat capacity of the probe would allow increased power to be utilized by the probe for ultrasound signal emission to significantly improve the quality of the resulting images obtained by the probe. The improved heat capacity can also enable the probe to be operated for longer periods of time and/or operated at higher ambient environment temperatures.

BRIEF DESCRIPTION OF THE DISCLOSURE

In one exemplary embodiment of the disclosure, an ultrasound imaging probe includes an imaging device including at least one heat generating component, and at least one a thermal energy storage insert spaced from and disposed in thermal contact with the imaging device, the at least one a thermal energy storage insert containing a phase change material (PCM) therein.

According to another exemplary embodiment of the disclosure, a method of forming an ultrasound imaging probe includes the steps of manufacturing a thermal energy storage insert from a thermally conductive material, filling the thermal energy storage insert with a phase change material (PCM) and positioning the thermal energy storage insert within an interior of the probe.

According to a further exemplary embodiment of the disclosure, an ultrasound imaging system includes a processing unit configured to receive and process acquired ultrasound image data to create ultrasound images derived from the ultrasound image data, a display operably connected to the processing unit to present the created ultrasound images to a user and an ultrasound imaging probe operably connected to the processing unit to obtain the ultrasound image data, the ultrasound imaging probe having an imaging device and at least one thermal energy storage insert spaced from and disposed in thermal contact with the imaging device within the probe, the at least one thermal energy storage insert containing a phase change material (PCM) therein, wherein the thermal energy storage insert is manufactured to closely conform to a shape of a space defined within the interior of the probe.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
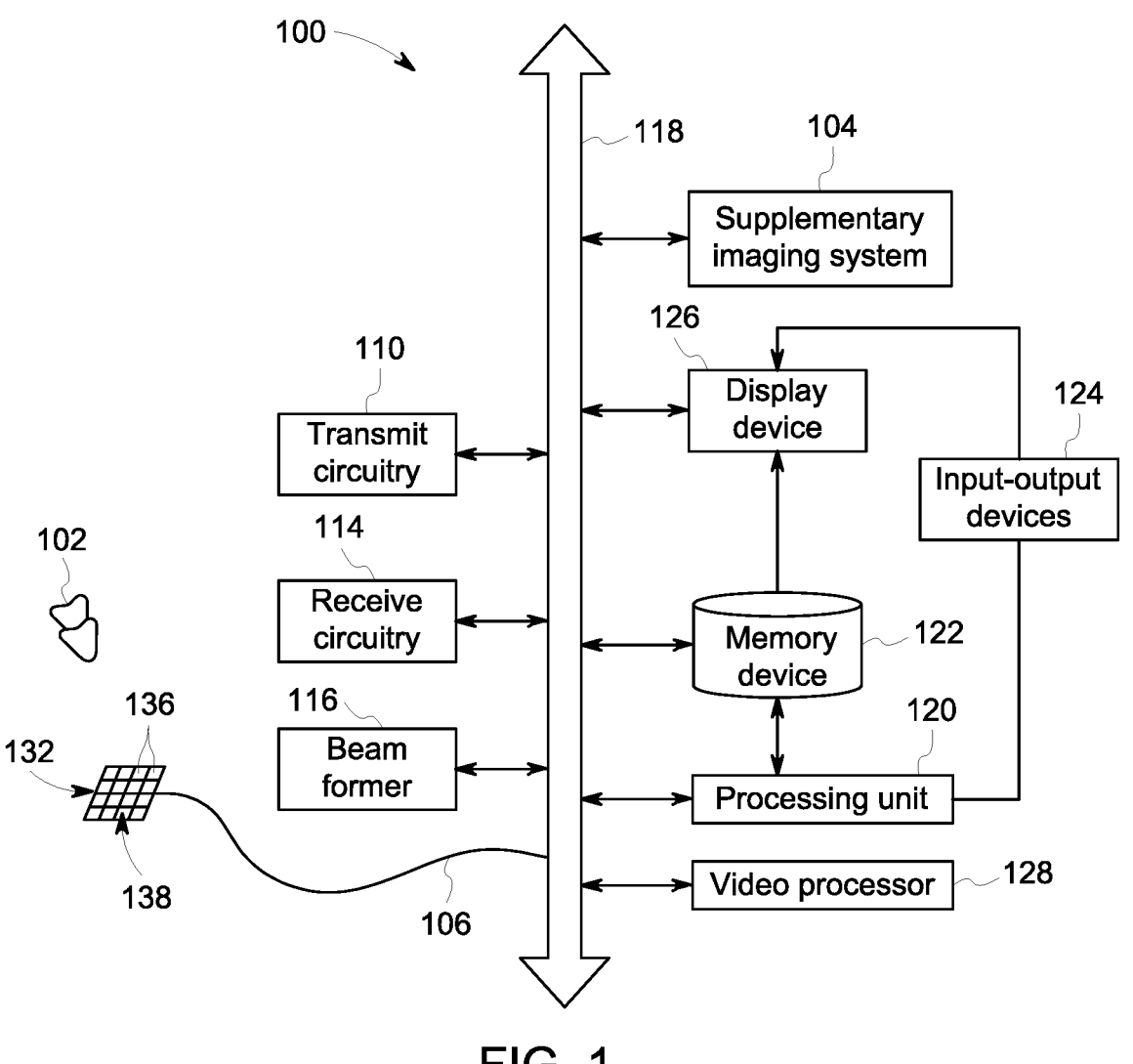
FIG. 1 is a schematic view of an ultrasound imaging system according to an embodiment of the disclosure.

FIG. 1 illustrates an exemplary ultrasound imaging system 100 for optimal visualization of a target structure 102 for use during ultrasound imaging procedures. For discussion purposes, the system 100 is described with reference to a TEE probe utilized with the system 100. However, in certain embodiments, other types of imaging probes may be employed with the imaging system 100, such as a TTE probe, or an ICE probe, among others.

In one embodiment, the ultrasound imaging system 100 employs ultrasound signals to acquire image data corresponding to the target structure 102 in a subject. Moreover, the ultrasound imaging system 100 may combine the acquired image data corresponding to the target structure 102, for example the cardiac region, with supplementary image data. The supplementary image data, for example, may include previously acquired images and/or real-time intra-operative image data generated by a supplementary imaging system 104 such as a CT, MRI, PET, ultrasound, fluoroscopy, electrophysiology, and/or X-ray system. Specifically, a combination of the acquired image data, and/or supplementary image data may allow for generation of a composite image that provides a greater volume of medical information for use in accurate guidance for an interventional procedure and/or for providing more accurate anatomical measurements.

Accordingly, in one embodiment shown in FIG. 1, the ultrasound imaging system 100 includes an interventional device or probe, such as an ultrasound imaging probe 106, a laparoscope, a bronchoscope, a colonoscope, a needle, a catheter and/or an endoscope. The ultrasound imaging probe 106 is adapted for external use, i.e., the probe 106 is placed on the skin of the patient to image internal structures of the patient, or the probe 106 can be configured to be operated in a confined medical or surgical environment such as a body cavity, orifice, or chamber corresponding to a subject, e.g., the patient.

To that end, in certain embodiments shown in FIG. 1, the ultrasound imaging system 100 includes transmit circuitry 110 that may be configured to generate a pulsed waveform to operate or drive an imaging device 132, which includes one or more transducer elements 136 or a transducer array 138, as controlled by the user via the system 100, or a control device or handle (not shown) operatively connected to the imaging device 132 as part of the system 100. The transducer elements 136 are configured to transmit and/or receive ultrasound energy and may comprise any material that is adapted to convert a signal into acoustic energy and/or convert acoustic energy into a signal. For example, the transducer elements 136 may be a piezoelectric material, such as lead zirconate titanate (PZT), or a capacitive micromachined ultrasound transducer (CMUT) according to exemplary embodiments. The interventional device/ultrasound imaging probe 106 may include more than one transducer element 136, such as two or more transducer elements 136 optionally arranged in a matrix transducer array 138 or separated from each other on the interventional device/ultrasound imaging probe 106. The transducer elements 136 produce echoes that return to the transducer elements 136/array 138 and are received by receive circuitry 114 for further processing. The receive circuitry 114 may be operatively coupled to a beamformer 116 that may be configured to process the received echoes and output corresponding radio frequency (RF) signals.

Further, the system 100 includes a processing unit 120 communicatively coupled to the beamformer 116, the interventional device/ultrasound imaging probe 106, and/or the receive circuitry 114, over a wired or wireless communications network 118. The processing unit 120 may be configured to receive and process the acquired image data, for example, the RF signals according to a plurality of selectable ultrasound imaging modes in near real-time and/or offline mode.

Moreover, in one embodiment, the processing unit 120 may be configured to store the acquired volumetric images, the imaging parameters, and/or viewing parameters in a memory device 122. The memory device 122, for example, may include storage devices such as a random access memory, a read only memory, a disc drive, solid-state memory device, and/or a flash memory. Additionally, the processing unit 120 may display the volumetric images and or information derived from the image to a user, such as a cardiologist, for further assessment on a operably connected display 126 for manipulation using one or more connected input-output devices 124 for communicating information and/or receiving commands and inputs from the user, or for processing by a video processor 128 that may be connected and configured to perform one or more functions of the processing unit 120. For example, the video processor 128 may be configured to digitize the received echoes and output a resulting digital video stream on the display device 126.

Looking now at the exemplary illustrated embodiment of FIGS. 2-5, the ultrasound imaging probe 106, such as a transthoracic echocardiography (TTE) probe, is connected to the imaging system 100 and is operable via the system 100 or a control handle (not shown) to control the function and/or movement of the ultrasound imaging probe 106. The ultrasound imaging probe 106 includes a handle/housing 131 to which includes a first end 130 that includes the imaging device 132 and a second end 134 that is connected to signal transmission and control/power wiring 135 extending between the system 100 and the ultrasound imaging probe 106 to control the operation of the imaging device 132.

Figure 2:
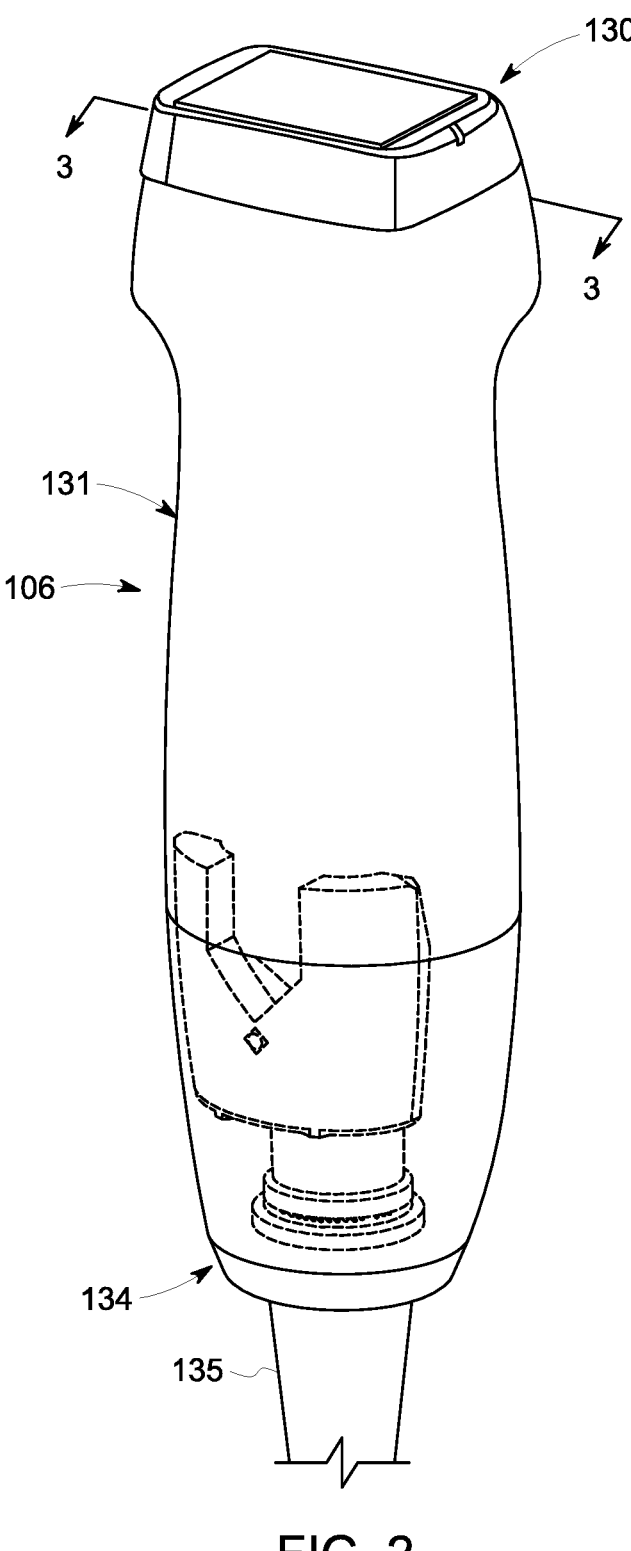
FIG. 2 is an isometric view of an ultrasound probe according to an exemplary embodiment of the disclosure.
Figure 3:
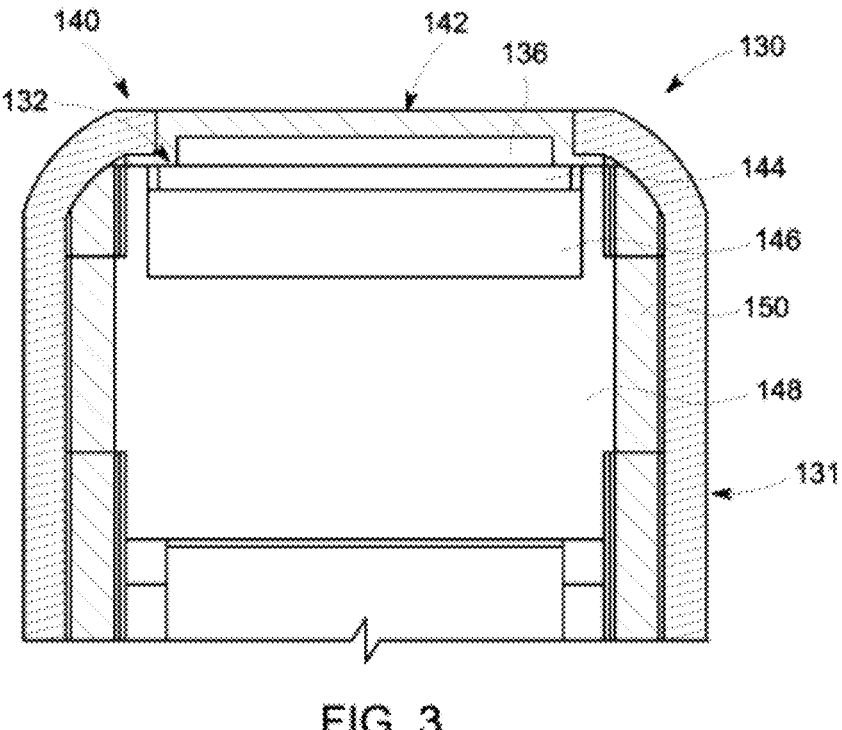
FIG. 3 is a cross-sectional view along line 3-3 of FIG. 2.
Figure 4:
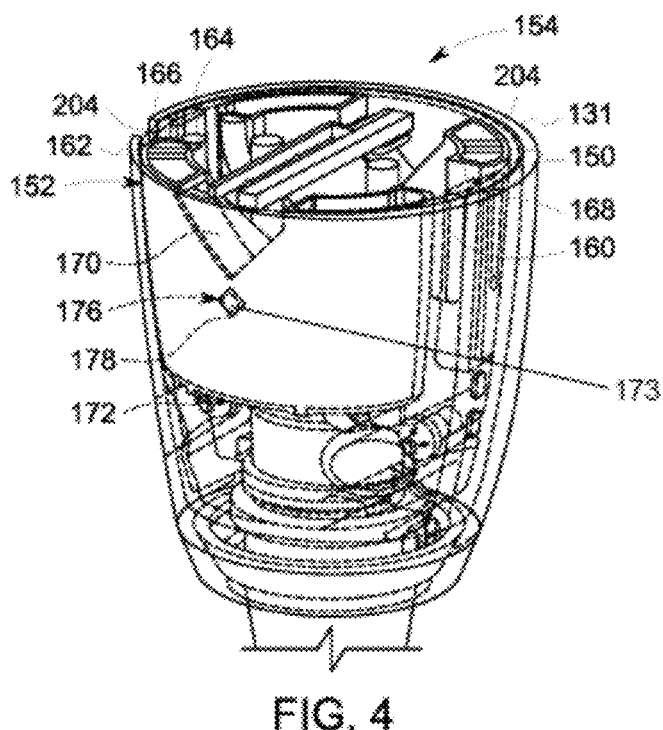
FIG. 4 is partially broken away, isometric view of the probe of FIG. 2
Figure 5:
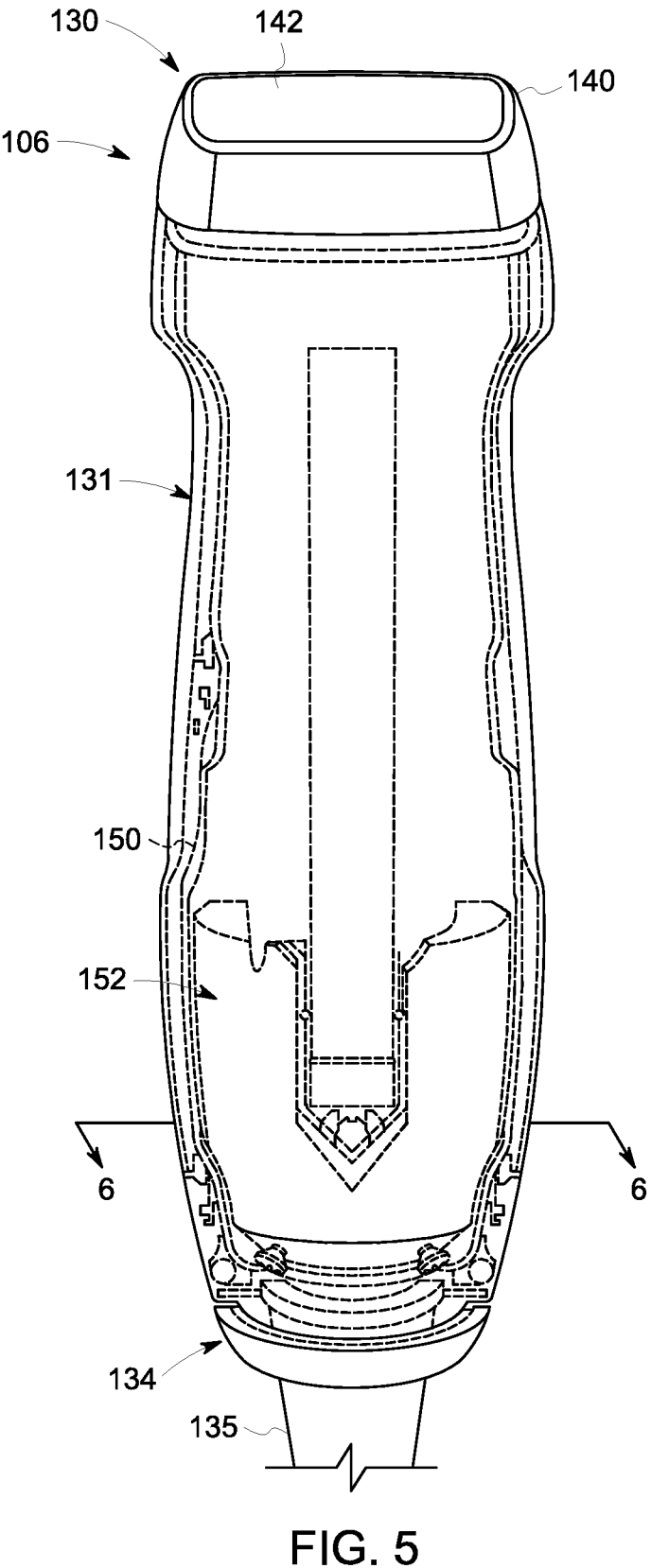
FIG. 5 is partially broken away view of an ultrasound probe according to an alternative embodiment of the disclosure.
Figure 6:
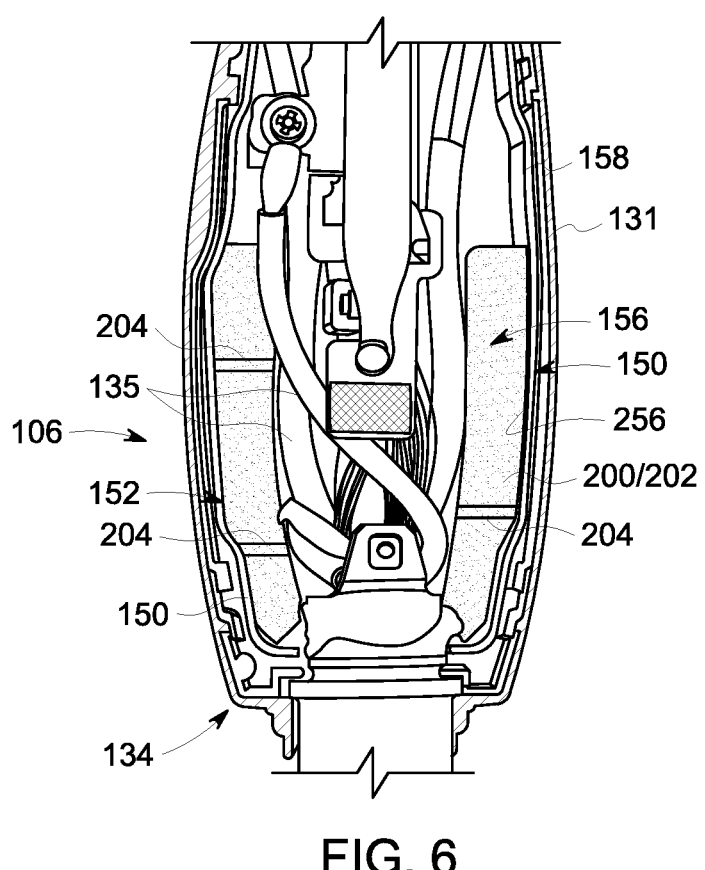
FIG. 6 is a cross-sectional view along line 6-6 of FIG. 5.
Figure 7:
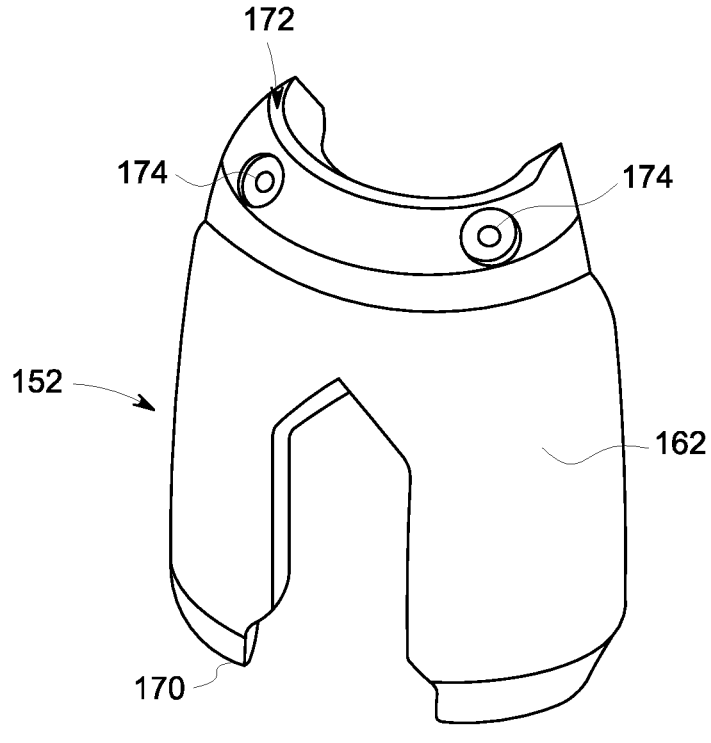
FIG. 7 is an isometric view of one exemplary embodiment of a heat energy storage insert disposed within the probe of FIG. 5.

As shown in the exemplary embodiment of FIGS. 2 and 3, the imaging device 132 is disposed at the first end 130 adjacent a cover 140 disposed over the transducer elements 136/array 138 formed with an acoustic lens 142. The lens 142 enables the ultrasound signals emitted from and received by the transducer elements 136/array 138 to pass unobstructed through the housing 131.

The imaging device 132 may be configured to generate cross-sectional images of the target structure 102 for evaluating one or more corresponding characteristics. Particularly, in one embodiment, imaging device 132 is configured to acquire a series of three-dimensional (3D) and/or four-dimensional (4D) ultrasound images corresponding to the subject, though the imaging device 132 can also obtain one-dimensional (1D) and two-dimensional (2D) ultrasound images. In certain embodiments, the imaging system 100 may be configured to generate the 3D model relative to time, thereby generating a 4D model or image corresponding to the target structure, such as the heart of the patient. The imaging system 100 may use the 3D and/or 4D image data, for example, to visualize a 4D model of the target structure 102 for providing a medical practitioner with real-time guidance for navigating the ultrasound imaging probe/interventional device 106 on or within the patient.

Looking now at FIGS. 2-3, the imaging device 132 includes an application-specific integrated circuit (ASIC) 144 connected between the transducer elements 136/array 138 and the power/control wiring 135 to control the operation of the imaging device 132 using power and control signals transmitted from the imaging system 100 via the wiring 135. The ASIC 144 is connected to/supported by an acoustic backing layer 146 that, in turn, is connected to a heat sink 148. In operation, heat generated by the imaging device 132, i.e., the transducer elements 136/array 138 and the ASIC 144, is conducted away from the imaging device 132 through the housing 131 such as directly through the acoustic lens 142 or through the acoustic backing layer 146 to the heat sink 148. The heat sink 148 is thermally coupled between the imaging device 132 and the housing 131, e.g., by a heat spreader 150 formed of a pair of opposed halves joined to one another within the housing 131 which extend from the cover 140 to the second end 134 to dissipate heat from the imaging device 132 and heat sink 148 along the length of the handle 131. The heat spreader 150 can also function as an electromagnetic interference (EMI) shield.

To assist in the absorption, storage or collection, and dissipation of the heat/thermal energy from the imaging device 132, the ultrasound imaging probe 106 further includes one or more heat/thermal energy storage or collecting inserts 152 located within the housing 131, as best shown in FIGS. 2 and 4-7. The inserts 152 are positioned within the housing 131 and a heat/thermal energy storage material 156 (FIG. 6) is located within the insert 152. Each insert 152 is constructed to conform to the interior space 158 defined between the housing 131/the heat spreader 150 and the other internal components of the ultrasound imaging probe 106, e.g., the imaging device 132 and wiring 135.

To enable the insert 152 to closely conform to the shape of the space 158, the insert 152 is manufactured to closely control the tolerances of the shape and thickness of the various walls or other components of the insert 152. To accomplish this close conformance of the insert 152 with the space 158, any of a number of suitable manufacturing processes can be employed, such as casting, molding, forming, cutting, joining, and combinations thereof with some processes requiring multiple steps and parts to form the desired hollow insert 152. In one particular exemplary embodiment, the insert 152 is formed in an additive manufacturing process, including but not limited to powder bed fusion methods including Electron Beam Melting (EBM), Direct Metal Laser Sintering (DMLS), Direct Metal Laser Melting (DMLM), Selective Laser Sintering (SLS), and Binderjet method.

As shown in the exemplary embodiments of FIGS. 2 and 4-7, the insert 152 is formed to define an enclosed volume 160 and includes a front wall 162 and a rear wall 164 connected by side walls 166,168 and by each of a top wall 170 and a bottom wall 172. The shapes of the various walls 162-172 may contain or be formed with any shape, curvature or other contours in order to fit within the interior space 158 of the housing 131/heat spreader 150. As the walls 162-172 in the illustrated exemplary embodiment of the insert 152 are additively manufactured, there are no seams or gaps between the respective walls 162-172. Alternatively, any gaps or seams in an insert 152 formed using a different process according to another embodiment can be suitably sealed using various techniques or materials, such as welds and adhesives, among others.

In addition to conforming to the shape of the space 158 defined within the housing 131/heat spreader 150, the insert 152 can be formed with one or more alignment features 176 in one or more of the walls 162-172 that can engage the housing 131/heat spreader 150 or other portions of the ultrasound imaging probe 106 in order to properly seat and/or constrain the movement of the insert 152 within the ultrasound imaging probe 106. The features 176 can have any suitable shape, and in the illustrated embodiment of FIGS. 2 and 4, the insert 152 can include an aperture 178. The aperture 178 is shaped to accommodate a pin or tab 173 disposed on the housing 131/heat spreader 150 to properly seat and align the insert 152 relative to the housing 131/heat spreader 150. To retain the insert 152 in the desired position within the ultrasound imaging probe 106 relative to the housing 131/heat spreader 150, the insert 152 is affixed to the housing 131/heat spreader 150, such as an interior surface 256 of the heat spreader 150, in any suitable manner, such as by using a mechanical fastener, e.g., tab 173, an adhesive, or combinations thereof, to maintain the connection of the insert 152 to the housing 131/150 and/or the heat sink 148 for effective heat transfer through the heat sink 148 and/or housing 131/heat spreader 150 to the heat/thermal energy collecting and storage material 156 within the insert 152.

In order to enable the heat collection and storage material 156 to be inserted within the volume 160 of the insert 152, in certain exemplary embodiments at least one of the walls 162-172, such as bottom wall 170, is formed with a number of ports 174 that extend through the wall 170 into communication with the interior volume 160 of the insert 152. The ports 174 enable the heat collection and storage material 156 to be inserted within the volume 160 through one or more of the ports 174, while air simultaneously exits/is forced out of the volume 160 through another port 174.

With regard to the form or type of the heat collection and storage material 156, the material 156 can be selected from any suitable material capable of insertion within the volume 160 of the insert 152 and of absorbing/collecting and storing heat to provide the desired increased heat capacity/heat retaining/thermal management function of the insert 152. In one exemplary embodiment the heat collecting and storage material 156 is selected to be a phase change material 200 (PCM) which is a substance which absorbs sufficient energy at a phase transition of the PCM to provide cooling, with the phase change being between solid and liquid. By melting at the phase change temperature (PCT) for the PCM 200 when thermally contacted by heat generated by the imaging device 132, the PCM 200 is capable of absorbing and storing large amounts of heat/thermal energy transmitted from the imaging device 132 to the PCM 200 through the heat sink 148 and/or the heat spreader 150. Heat from the heat sink 148 and/or heat spreader 150 is absorbed by the PCM 200 when the PCM 200 changes from solid to liquid and can be released as the PCM 200 cools and changes from a liquid to a solid, such as when the ultrasound imaging probe 106 is not in operation. The PCM 200 can be selected from an inorganic, organic PCM, metallic PCM, eutectic alloys etc., with the organic PCM 200 being derived either from petroleum, from plants or from animals, such as paraffin waxes, etc., among others. In one exemplary embodiment, the PCM 200 is selected to be a paraffin with a PCT of approximately 32° C.

However, in certain exemplary embodiments, the selection of the PCM 200 for use in the insert 152 can be dependent upon the location of the insert 152 within the ultrasound imaging probe 106 to lower the thermal resistance between the heat generating components and PCM. In particular, the PCM 200 can be selected so that the PCM 200 completes its melting cycle just prior to the patient contact surface/lens 142 reaching the maximum allowable regulatory temperature of 43° C. For example, as the maximum allowable temperature of the lens 142 limits the operation of the ultrasound imaging probe 106, and the insert 152/PCM 200 is located at the opposite end of the probe 106 where there is a known thermal resistance that results in a ΔT known temperature drop from the lens 142 to the insert 152/PCM 200, then the PCM 200 should be selected to be a material that complete its melting process at a temperature corresponding to the known ΔT. In this manner, the thermal resistance to the PCM 200 is accounted for in maximizing the operational time extension for the use of the ultrasound imaging probe 106 with the insert 152/PCM 200. Alternatively, in situations where the insert 152/PCM 200 is positioned closer to the lens 142, the known thermal resistance between the lens 142 and the position of the insert 152/PCM 200 can be employed to determine the PCM 200 having a PCT/melting point that lowers ΔT, thereby maximizing the operating time of the ultrasound imaging probe 106 before the lens 142 exceeds the maximum allowable temperature.

Figure 13A:
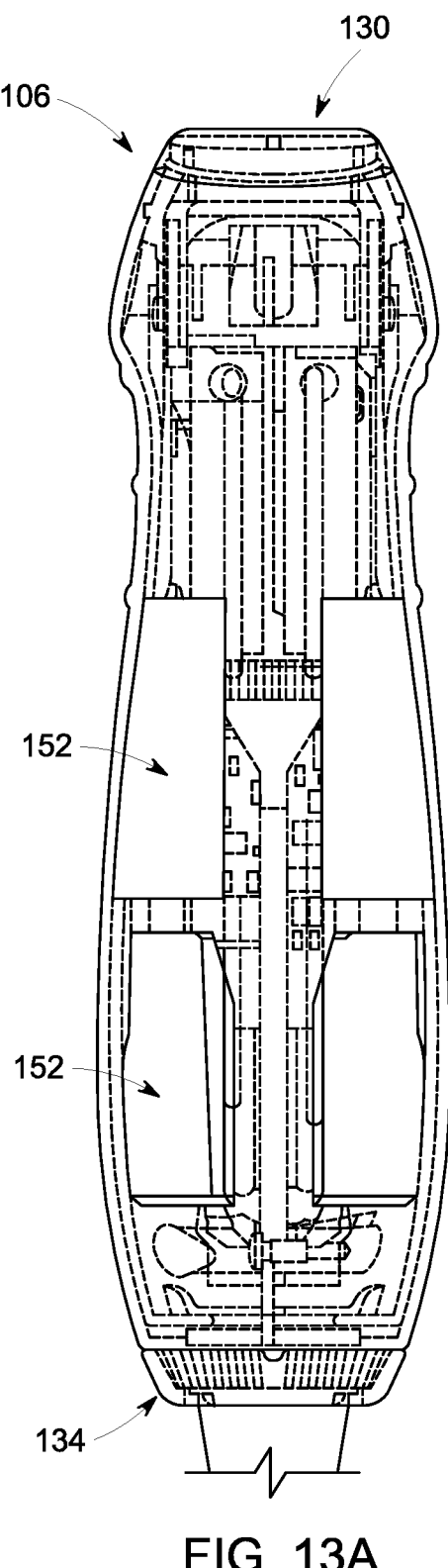
FIGS. 13A-13B are partially broken away isometric views of another exemplary embodiment of a heat energy storage insert disposed within the probe of FIG. 5.
Figure 13B:
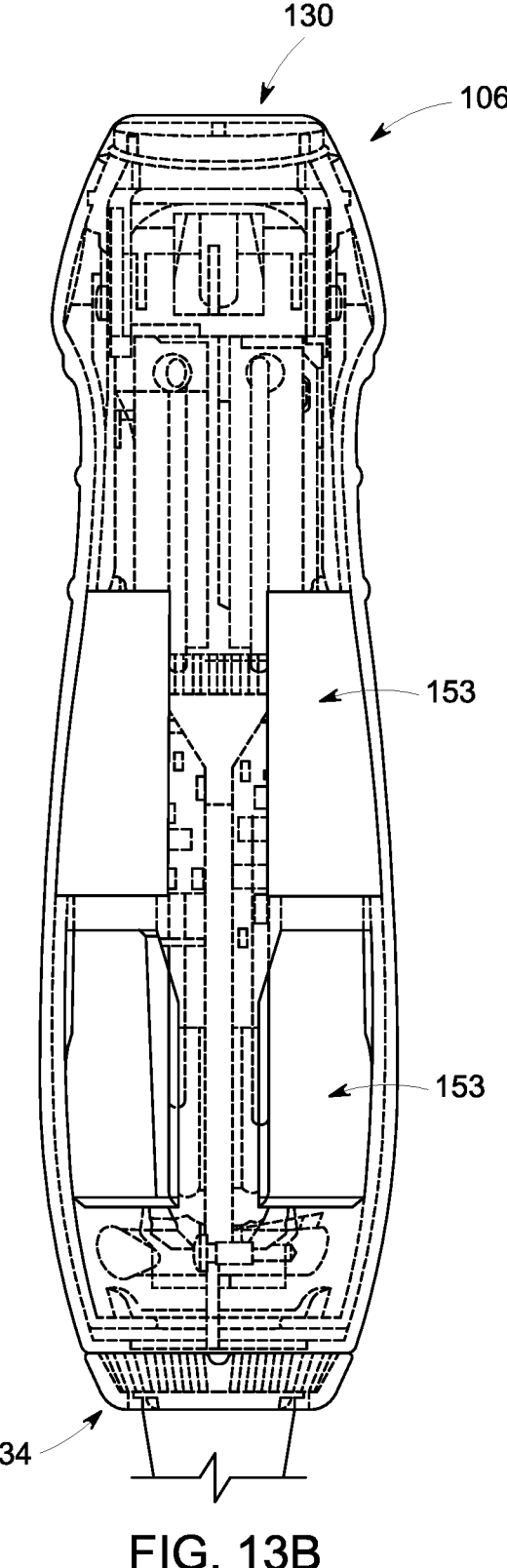

In particular, when looking at the illustrated exemplary embodiments of FIGS. 13A-13B, the ultrasound imaging probe 106 can include inserts 152 incorporated at multiple locations in the probe 106, with PCMs 200 disposed within the inserts 152 having different melting temperatures that are dependent on their location from the lens 142. The multiple PCM inserts 152 can be (A) physically separate inserts 152 (FIG. 13A), or a single insert 152 containing multiple chambers 153 (FIG. 13B) for containing different PCM 200/composite PCM material 202 (to be described) with different melting temperatures corresponding to the location of the particular volume 160 relative to the imaging device 132 and/or lens 142. More specifically, in the case of the single insert 152 containing multiple chambers 153 in FIG. 13B, the chambers 153 can be continuous or separated. In the case of separate chambers 153, each chamber 153 can contain the same PCM 200/202 or different PCMs 200/202 having different melting temperatures.

In one exemplary embodiment of a process for the insertion of the heat collection material 156 within the insert 152, particularly when a PCM 200 is used as the heat collection material 156, one or more of the following steps can be performed:

1. Weigh the insert 152 prior filling with the heat collection material 156 to back out mass of heat collection material 156 after completion of filling (optional);
2. Melt the heat collection material 156 to liquid state (e.g., >5° C. over PCT);
3. Heat the unfilled inserts 152 and filling devices, e.g., syringes so that the PCM 200 doesn't solidify during the filling process (optional);
4. Fill the syringe to the approximate available volume within insert 152;
5. Place the inserts 152 on a heated plate (not shown) or position the inserts 152 inside a heated environmental chamber (not shown) (optional);
6. Inject or otherwise introduce the PCM 200 into each insert 152, while avoiding overfilling (which can lead to excessive pressure build up during the PCM melting process where the volume expands when going from solid to liquid phases);
7. Seal the fill and return ports 174;
8. Weigh the filled inserts 152 again to estimate the mass of PCM 200 within the insert 152 (optional).

Figure 8:
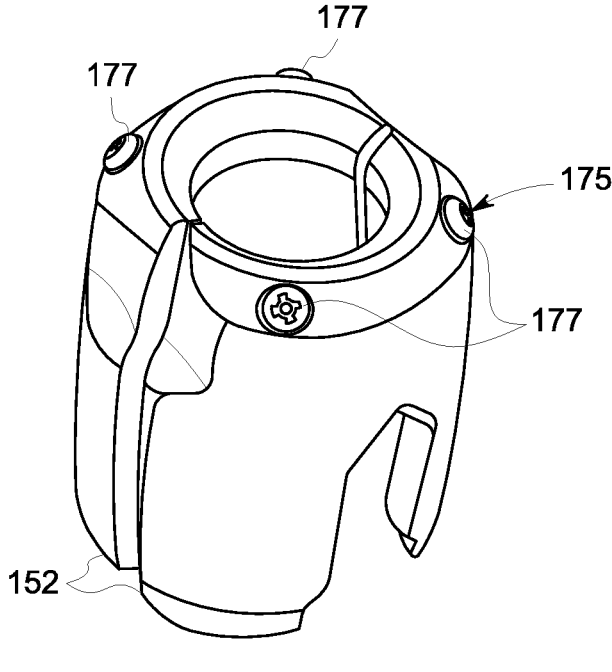
FIG. 8 is an isometric view of another exemplary embodiment of a heat or thermal energy storage insert disposed within the probe of FIG. 5.
Figures 9A, 9B:
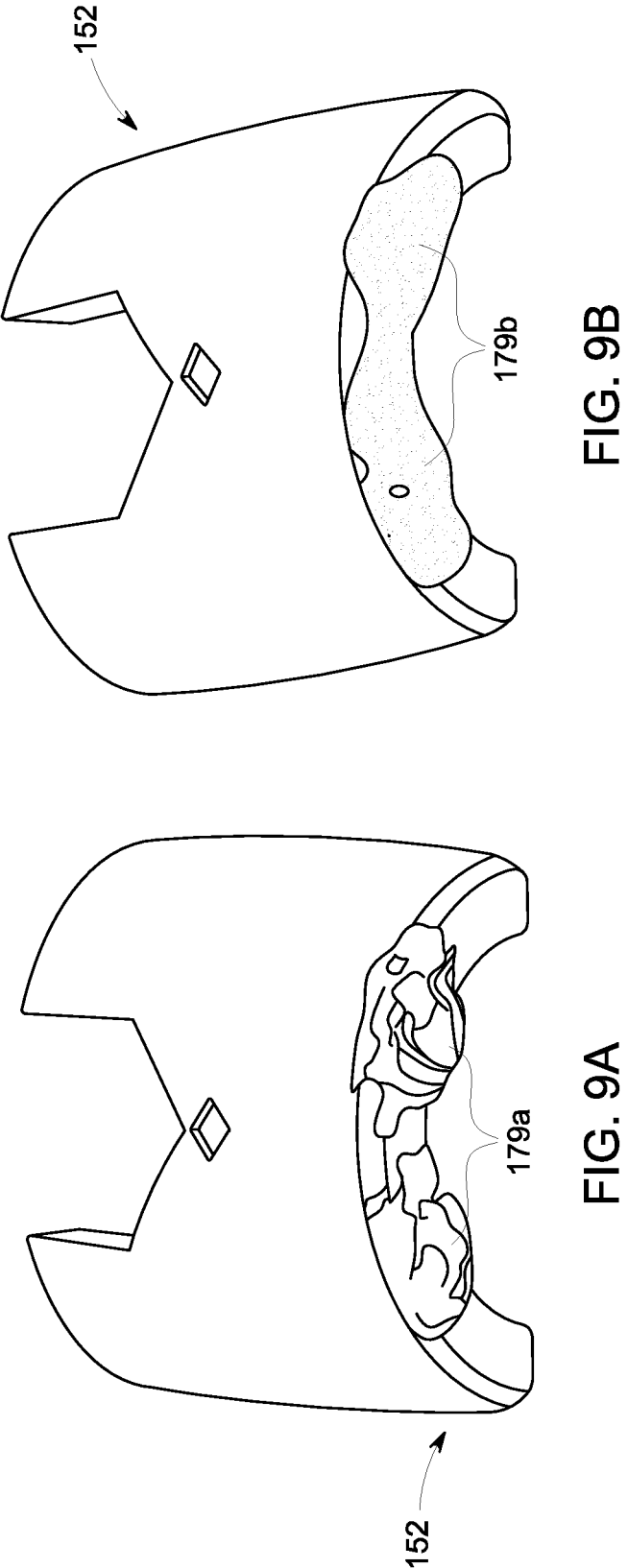
FIGS. 9A-9B are isometric views of alternative closures for the heat energy storage insert of FIG. 7.

Referring to FIGS. 8-9, once the heat collection material 156 is disposed within the volume 160, the ports 174 can be closed or sealed, either releasably or permanently, by suitable closures 175 positioned over and/or within the ports 174. The closures 175 can have any suitable form, including, for example, O-ring sealed screws 177 (FIG. 8), or permanently sealing with a thermal adhesive 179a and/or epoxy 179b (FIG. 9), soldering, welding, riveting, or clamping, among others.

As an alternative to the PCM 200, the heat collection material 156 can be a composite PCM material 202. The composite PCM material 202 is formed of a PCM material enclosed within another encapsulating material. e.g., such as to form particles, that are supported within a matrix material or continuous phase. The encapsulating material in certain embodiments is selected to have a high mechanical strength or elasticity in order maintain the encapsulation of the PCM material within the encapsulating material as the PCM material expands upon melting and contracts upon freezing. In a particular exemplary embodiment, the composite PCM material 202 is a microencapsulated PCM where microscopic PCM particle is enclosed within a protective coating as the encapsulating material, such as a polymer coating, that enables the phase change of the PCM particle to be retained completely within the coating.

The matrix material supporting the microencapsulated PCM material/particles is preferably selected from a high thermal conductivity material that enables heat to readily reach the PCM material/particles within the matrix material. The use of a fluid as the continuous phase forms a slurry that can be introduced into the insert 152 in a manner similar to the PCM material 200 in liquid form, but consequently requires sealing of the ports 174 in a similar manner. Alternatively, if the matrix material or continuous phase is formed of an epoxy, silicone matrix or other similar material, the matrix material forms a solid within the volume 160 of the insert 152 that does not flow when the microencapsulated PCM undergoes a phase change from heat flowing from the imaging device 132. This can also be the case when the microencapsulated PCM is employed without a matrix material or continuous phase. Thus, use of the solid matrix material/continuous phase, thus forming a composite PCM 202, does not require that the insert 152 be sealed after placement within insert 152.

The materials utilized to construct the insert 152 can be selected as desired, and are materials that provide the desired rigidity to the insert 152 to retain the heat collection material 156 therein, while also enabling heat to be readily transmitted through the insert 152 to contact the heat collection material 156. In one particular exemplary embodiment, the material forming the insert 152 is selected from suitable metal materials, including but not limited to aluminum. In alternative exemplary embodiments, though metals offer improved thermal conductivity, the insert 152 could also be fabricated from non-metals, i.e. plastics having the necessary heat conductivity/transfer and structural properties i.e., higher thermal conductivity plastics formed as composites loaded with high thermal conductivity particles, or graphite, among others.

Further, the insert 152 can include internal support structures 204 (FIGS. 4 and 6) extending between various and/or opposed walls 162-172 of the insert 152 in order to both provide additional stability to the insert 152 and to enhance the thermal conductivity through the insert 152 to the PCM material 200 or composite PCM material 202 disposed within the volume 160 of the insert 152. These structures 204 can take various forms, such as lattices, posts, studs, fins and other similar structures extending between, or protruding from the walls 162-172 of the insert 152 while allowing the PCM material 200 or the composite PCM material 202 to be positioned around the structures to fill the volume 160.

Figure 10:
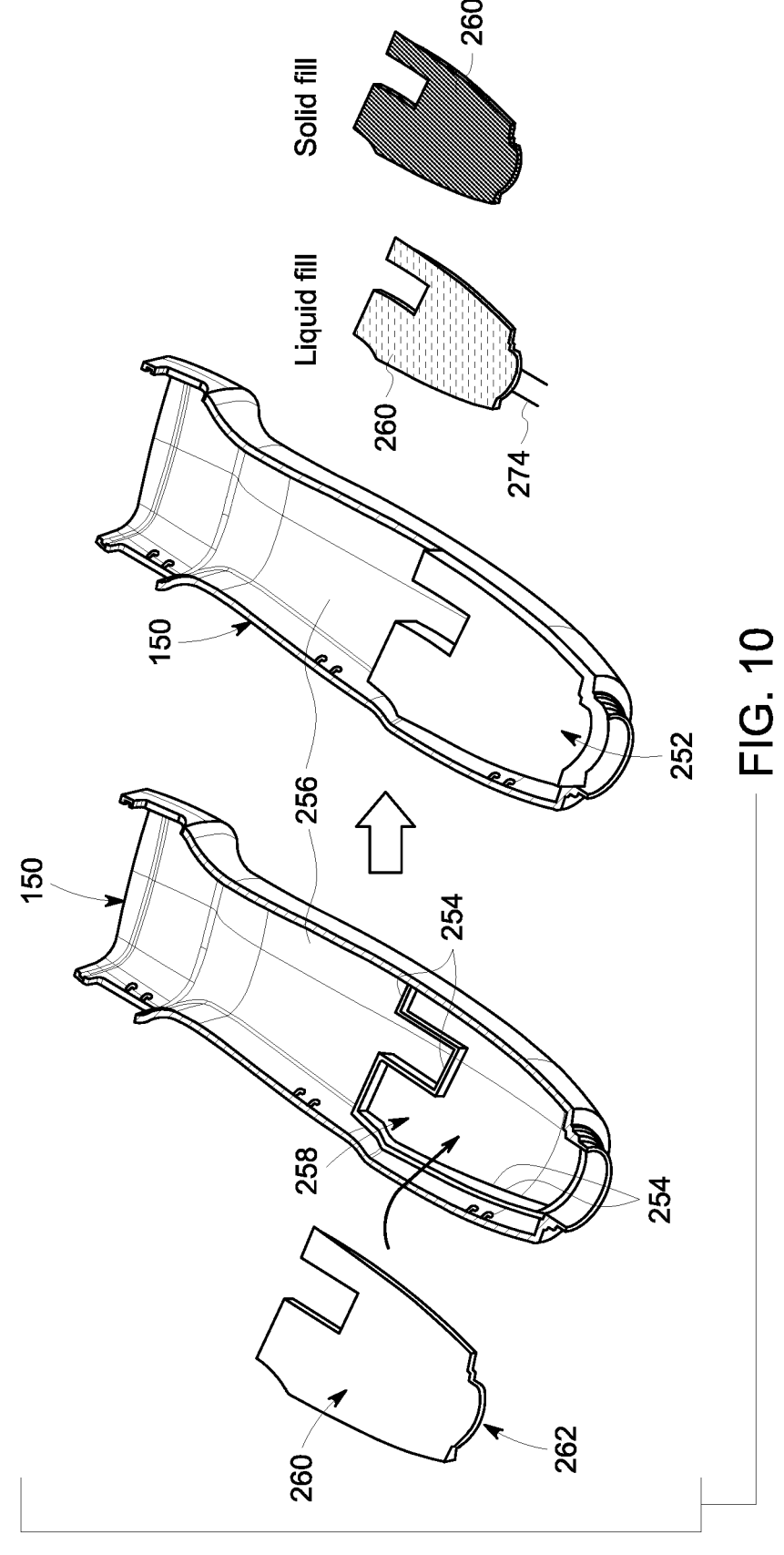
FIG. 10 is an isometric view of one exemplary embodiment of a heat energy storage insert disposed within the probe of FIG. 5.
Figure 11:
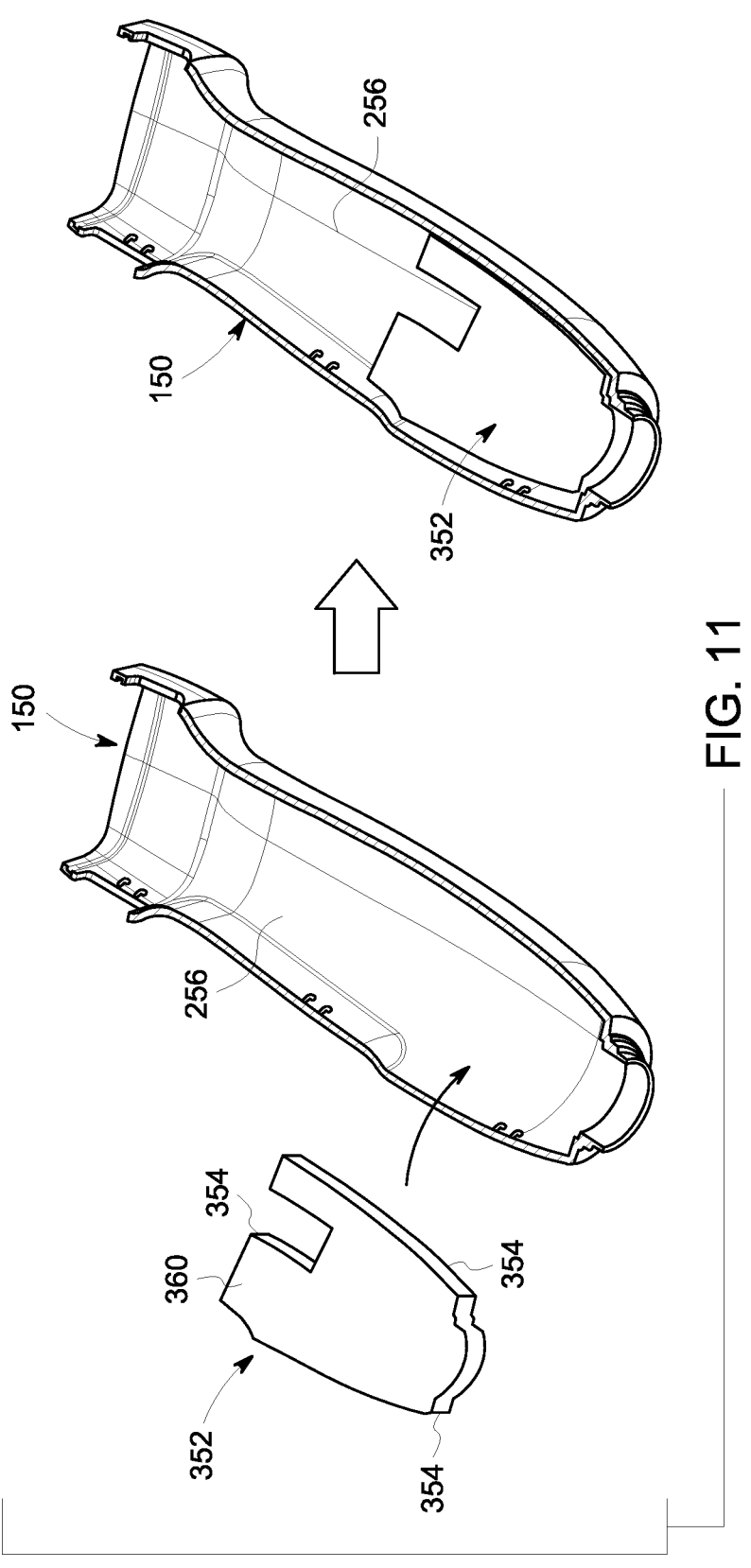
FIG. 11 is an isometric view of a further exemplary embodiment of a heat energy storage insert disposed within the probe of FIG. 5.
Figure 12:
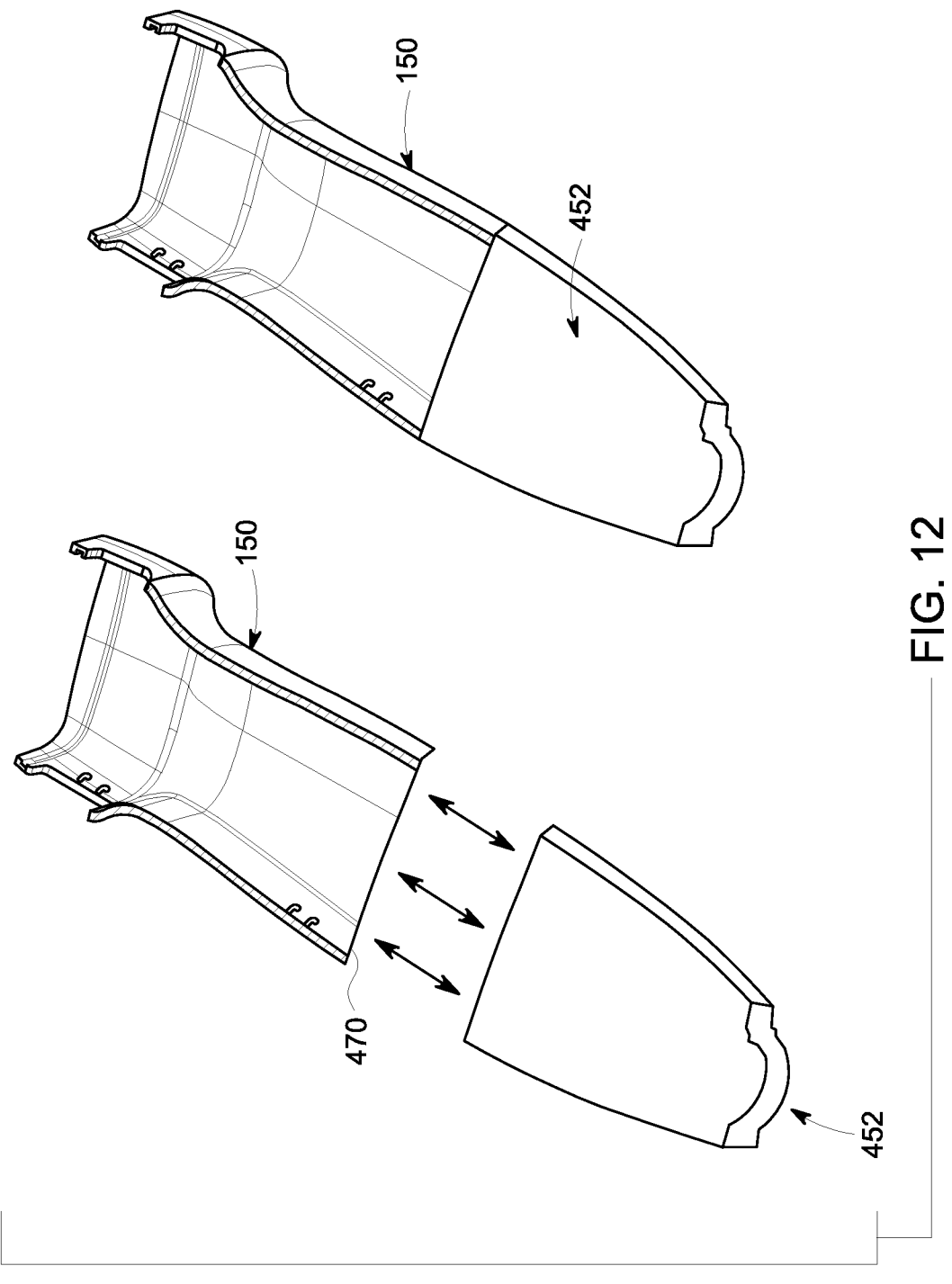
FIG. 12 is an isometric view of still a further exemplary embodiment of a heat energy storage insert disposed within the probe of FIG. 5.

Referring now to FIGS. 10-12, as an alternative to the insert 152 formed as a monolithic element formed separately from the ultrasound imaging probe 106 and mounted within the housing 131, another embodiment of the insert 152 can be formed in conjunction with the heat spreader 150.

Looking specifically at FIG. 10, the PCM insert 252 is formed by utilizing the existing heat spreader 150 to support one or more sidewalls 254 formed directly on an interior surface 256 of the heat spreader 150, either integrally with the heat spreader 150 or as a separate component attached to the interior surface 150, such as by welding, adhering and/or bonding the sidewalls 254 to the surface 256. Alternatively, to form the insert 252, the sidewalls 254 can be disposed on any other suitable surface of a component within the probe housing 131, e.g., the heat sink 148, or on the probe housing 131 itself. To enclose a volume 258 within the insert 252 within which the PCM 200/202 can be placed, a separate cover 260 having a perimeter 262 aligned with the sidewalls 254 is secured to the sidewalls 254 opposite the interior surface 256 to form an enclosed insert 252. The cover 260 can be sealed to the sidewalls 254 on the heat spreader 150 prior to filling with liquid PCM 200 through ports 274 formed on the cover 260, or a solid PCM 202 could be inserted into the volume 258 within the sidewalls 254 prior to sealing the cover 260 to the sidewalls 254 on the heat spreader 150. The cover 260 and sidewalls 254 can contain features (not shown) to facilitate sealing, such as tongue and groove features, or example.

Looking now at FIG. 11, in another alternative embodiment for the insert 352 formed similarly to the insert 252, the insert 352 includes a cover 360 to which is secured one or more sidewalls 354 that extend outwardly, e.g., perpendicularly, from the perimeter of the cover 360. The one or more sidewalls 354 are secured directly to the interior surface 256 of the heat spreader 150 to form the insert 352. Similarly to the embodiment of FIG. 10, the cover 360 can be sealed to the heat spreader 150 in any suitable manner, e.g., welding, adhering and/or bonding, optionally in conjunction with features (not shown) on the interior surface 256 of the heat spreader 150 to assist in securing the sidewalls 354 to the heat spreader 150. Further, the insert 352 can be filled with a liquid PCM 200 after securing the sidewalls 354 to the heat spreader 150, or solid/composite PCM 202 can be inserted into the volume 358 defined within the sidewalls 354 prior to sealing the sidewalls 354 to the heat spreader 150. In each of this embodiment of FIG. 11 and the embodiment of FIG. 10, utilizing the existing heat spreader 150 already forming a portion of the ultrasound imaging probe 106 as a portion of the PCM inserts 252,352 increases the volume 258,358 available for retaining the PCM 200/202 therein since a double wall is avoided at the PCM insert 252/352/heat spreader 150 interface. Also, similar to FIG. 10, the cover 360 and sidewalls 354 can be secured to any other suitable surface of a component within the probe housing 131, e.g., the heat sink 148, or on the probe housing 131 itself.

Referring now to FIG. 12, in another exemplary embodiment of the disclosure, the insert 452 is formed similarly to the embodiments of FIGS. 4-9, and is thermally bonded or otherwise secured directly to an end 470 of the heat spreader 150. However, the heat spreader 150 is shortened such that the insert 452 when bonded to the heat spreader 150 forms an extension of the heat spreader 150. The insert 452, either prior to or after bonding to the shortened heat spreader 150 can be filled with the liquid PCM material 200/composite PCM material 202. The insert 452 can be employed on one or both halves of the heat spreader 150 to provide the heat absorption from the PCM 200/202 disposed within the insert(s) 452. This embodiment of the insert 452 and spreader 150 allows for increased volume for the PCM 200/202 and weight savings as a result of the reduction of the material forming the heat spreader 150. Alternatively, the insert 452, or any other embodiment of the insert 152,252, 352 can be formed as a part of the housing 131, or any other suitable portion of the ultrasound imaging probe 106, such as a part of the backing layer 146 or the heat sink 148, among others. In addition, due to the additive manufacturing process employed in their construction, the inserts 152,252,352, 452 can be formed with:

1. a solid support structure aligned with cutoff direction to prevent breaking through the thin walls and thus enabling the thin-walled construction for the inserts 152,252,352,452;

2. self-supporting internal structure, with or without the internal support structures 204; and/or 3. the holes or ports 174 to allow de-powdering, filling with PCM 200/202, and sealing of the inserts 152,252, 352,452.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasound imaging probe comprising:

a housing formed of a layer of a thermally conductive material having an exterior surface and an interior surface defining an interior space therein and a tab extending inwardly from the interior surface into the interior space;

an imaging device disposed within the interior space of the housing and including at least one heat-generating component; and at least one thermal energy storage insert spaced from and disposed in thermal contact with the imaging device within the interior space of the housing, the at least one thermal energy storage insert containing a phase change material (PCM) therein, an alignment feature formed within a wall of the at least one thermal energy storage insert and adapted to engage and receive a mechanical fastener extending between the interior surface of the housing and the at least one thermal energy storage insert to align the at least one thermal energy storage insert with the housing, and an exterior shape that conforms to the interior space of the housings wherein the alignment feature is an aperture in the wall of the at least one thermal energy storage insert adapted to seat on the mechanical fastener of the housing to align the at least one thermal energy storage insert with the housing, wherein the mechanical fastener is formed as the tab located on and extending outwardly from the interior surface of the housing into the interior space of the housing for insertion within the aperture, and wherein the at least one thermal energy storage insert is additively manufactured to conform to a shape of the interior space of the housing.

2. The ultrasound imaging probe of claim 1, wherein the at least one thermal energy storage insert is additively manufactured without gaps between walls of the at least one thermal energy storage insert.

3. The ultrasound imaging probe of claim 1, wherein the at least one thermal energy storage insert is formed of an additively manufactured heat conducting material.

4. The ultrasound imaging probe of claim 1, further comprising a heat spreader disposed within the interior space of the housing in thermal contact with the imaging device, and wherein the at least one thermal energy storage insert is attached to the heat spreader.

5. The ultrasound imaging probe of claim 4, wherein the at least one thermal energy storage insert is formed as a part of the heat spreader.

6. The ultrasound imaging probe of claim 5, wherein at least one thermal energy storage insert comprises a cover directly attached to the heat spreader to define a volume between the cover and the heat spreader wherein the PCM is contained within the volume.

7. The ultrasound imaging probe of claim 1, wherein the PCM is selected from a liquid PCM and a composite PCM.

8. The ultrasound imaging probe of claim 1, wherein the at least one thermal energy storage insert comprises multiple chambers within the at least one thermal energy storage insert.

9. The ultrasound imaging probe of claim 8, wherein the multiple chambers are not connected to one another.

10. An ultrasound imaging system comprising:

a processing unit configured to receive and process acquired ultrasound image data to create ultrasound images derived from the ultrasound image data;

a display operably connected to the processing unit to present the created ultrasound images to a user; and an ultrasound imaging probe operably connected to the processing unit to obtain the ultrasound image data, the ultrasound imaging probe comprising:

a housing consisting of a layer of a thermally conductive material having an exterior surface and an interior surface defining an interior space therein, and a tab extending inwardly from the interior surface into the interior space;

an imaging device disposed within the interior space of the housing and including at least one heat-generating component; and at least one thermal energy storage insert spaced from and disposed in thermal contact with the imaging device within the interior space of the housing, the at least one thermal energy storage insert containing a phase change material (PCM) therein and an alignment feature formed within a wall of the at least one thermal energy storage insert and adapted to engage and receive a mechanical fastener extending between the interior surface of the housing and the at least one thermal energy storage insert to align the at least one thermal energy storage insert with the housing, wherein the thermal energy storage insert is manufactured with an exterior shape that conforms to the interior space of the housing, wherein the alignment feature is an aperture in the wall of the at least one thermal energy storage insert adapted to seat on the mechanical fastener of the housing to align the at least one thermal energy storage insert with the housing, wherein the mechanical fastener is formed as the located on and extending outwardly from the interior surface of the housing into the interior space of the housing for insertion within the aperture, and wherein the at least one thermal energy storage insert is additively manufactured to conform to a shape of the interior space of the housing.

11. The ultrasound imaging system of claim 10, wherein the at least one thermal energy storage insert is additively manufactured without gaps between walls of the at least one thermal energy storage insert.

* * * * *